(12) United States Patent
Sharma et al.

(10) Patent No.: US 11,087,862 B2
(45) Date of Patent: Aug. 10, 2021

(54) CLINICAL CASE CREATION AND ROUTING AUTOMATION

(71) Applicant: General Electric Company, Schenectady, NY (US)

(72) Inventors: Malvika Sharma, Pittsburgh, PA (US); Thomas C. Matus, South Park, PA (US); Shagun Grover, Santa Clara, CA (US)

(73) Assignee: General Electric Company, Schenectady, NY (US)

( * ) Notice: Subject to any disclaimer, the term of this patent is extended or adjusted under 35 U.S.C. 154(b) by 240 days.

(21) Appl. No.: 16/198,320

(22) Filed: Nov. 21, 2018

(65) Prior Publication Data

US 2020/0160941 A1    May 21, 2020

(51) Int. Cl.
*G16H 10/20* (2018.01)
*G16H 10/60* (2018.01)
*G16H 80/00* (2018.01)

(52) U.S. Cl.
CPC ............ *G16H 10/20* (2018.01); *G16H 10/60* (2018.01); *G16H 80/00* (2018.01)

(58) Field of Classification Search
CPC .......... G06N 3/008; G06N 3/02; G06N 3/063; G06N 3/08; G16H 50/20; G16H 30/40; G16H 50/30; G16H 80/00; G16H 10/60; G06F 40/16
See application file for complete search history.

(56) References Cited

U.S. PATENT DOCUMENTS

| | | |
|---|---|---|
| 7,702,524 B1 | 4/2010 | Whibbs et al. |
| 9,959,386 B2 | 5/2018 | Ohad et al. |
| 9,984,205 B2 | 5/2018 | Ohad et al. |
| 10,037,410 B2 | 7/2018 | Ohad et al. |
| 10,410,016 B1 * | 9/2019 | Damick .............. G06F 21/6209 |
| 2004/0039757 A1 | 2/2004 | McClure |
| 2005/0209885 A1 | 9/2005 | Lamb et al. |
| 2006/0047537 A1 | 3/2006 | Brimdyr |
| 2007/0027717 A1 | 2/2007 | Karamchedu et al. |

(Continued)

OTHER PUBLICATIONS

United States Patent and Trademark Office, "Non-Final Office Action," issued in connection with U.S. Appl. No. 14/188,354, dated Oct. 7, 2015, 33 pages.

(Continued)

*Primary Examiner* — Maroun P Kanaan
(74) *Attorney, Agent, or Firm* — Hanley, Flight & Zimmerman, LLC

(57) ABSTRACT

Systems, methods, and apparatus providing automated clinical case creation and routing are disclosed and described. An example cloud-based medical image and document exchange infrastructure apparatus includes an instruction processor to execute an instruction to process data according to one or more defined rules, wherein the instruction is associated with a state, the state including at least active and inactive. The example apparatus also includes a gateway to at least: receive incoming data related to an imaging study; monitor the incoming data to compare the incoming data to one or more active instructions; and, when an active instruction applies to the incoming data, execute the active instruction with respect to the corresponding imaging study.

20 Claims, 12 Drawing Sheets

(56) References Cited

U.S. PATENT DOCUMENTS

| | | |
|---|---|---|
| 2007/0083403 A1 | 4/2007 | Baldwin et al. |
| 2007/0143148 A1 | 6/2007 | Kol et al. |
| 2008/0103829 A1 | 5/2008 | Mankopf et al. |
| 2011/0010200 A1 | 1/2011 | Firozvi et al. |
| 2011/0022812 A1 | 1/2011 | van der Linden et al. |
| 2011/0191122 A1 | 8/2011 | Kharraz Tavakol et al. |
| 2012/0035959 A1 | 2/2012 | Berdia |
| 2012/0130781 A1 | 5/2012 | Li |
| 2012/0173285 A1 | 7/2012 | Muthukrishnan |
| 2012/0203094 A1 | 8/2012 | Suri |
| 2012/0303814 A1 | 11/2012 | Ferris |
| 2013/0005374 A1 | 1/2013 | Uusitalo et al. |
| 2013/0097127 A1 | 4/2013 | Mohapatra et al. |
| 2013/0110537 A1 | 5/2013 | Smith |
| 2013/0132104 A1 | 5/2013 | Wood-Salomon et al. |
| 2013/0132109 A1 | 5/2013 | Mruthyunjaya et al. |
| 2013/0179192 A1 | 7/2013 | Rejendran et al. |
| 2013/0191161 A1 | 7/2013 | Churchwell et al. |
| 2013/0208966 A1 | 8/2013 | Zhao et al. |
| 2013/0227670 A1 | 8/2013 | Ahmad et al. |
| 2013/0272587 A1* | 10/2013 | Fang ............ H04N 19/60 382/128 |
| 2013/0282397 A1 | 10/2013 | Easterhaus et al. |
| 2013/0325503 A1 | 12/2013 | Abrahams et al. |
| 2014/0026194 A1 | 1/2014 | Smith |
| 2014/0067758 A1 | 3/2014 | Boldyrev et al. |
| 2014/0074638 A1 | 3/2014 | Shah |
| 2014/0114672 A1 | 4/2014 | Wright et al. |
| 2014/0223507 A1 | 8/2014 | Xu |
| 2014/0324457 A1 | 10/2014 | Kim et al. |
| 2014/0372149 A1 | 12/2014 | Friese et al. |
| 2015/0019009 A1 | 1/2015 | Feldman et al. |
| 2015/0073951 A1 | 3/2015 | Ladd et al. |
| 2015/0149196 A1 | 5/2015 | Ohad et al. |
| 2015/0149211 A1 | 5/2015 | Ohad et al. |
| 2015/0347682 A1* | 12/2015 | Chen ............ G16H 50/20 705/2 |
| 2018/0032997 A1* | 2/2018 | Gordon ............ G06Q 30/0269 |
| 2018/0247201 A1* | 8/2018 | Liu ............ G06N 3/088 |

OTHER PUBLICATIONS

United States Patent and Trademark Office, "Final Office Action," issued in connection with U.S. Appl. No. 14/188,354, dated Apr. 18, 2016, 34 pages.

United States Patent and Trademark Office, "Advisory Action," issued in connection with U.S. Appl. No. 14/188,354, dated Jul. 5, 2016, 5 pages.

United States Patent and Trademark Office, "Non-Final Office Action," issued in connection with U.S. Appl. No. 14/188,354, dated Jul. 7, 2017, 35 pages.

United States Patent and Trademark Office, "Notice of Allowance," issued in connection with U.S. Appl. No. 14/188,354, dated Dec. 26, 2017, 10 pages.

United States Patent and Trademark Office, "Non-Final Office Action," issued in connection with U.S. Appl. No. 14/188,275, dated Apr. 7, 2016, 36 pages.

United States Patent and Trademark Office, "Final Office Action," issued in connection with U.S. Appl. No. 14/188,275, dated Sep. 23, 2016, 35 pages.

United States Patent and Trademark Office, "Non-Final Office Action," issued in connection with U.S. Appl. No. 14/188,275, dated Jul. 28, 2017, 36 pages.

United States Patent and Trademark Office, "Notice of Allowance," issued in connection with U.S. Appl. No. 14/188,275, dated Jan. 4, 2018, 13 pages.

United States Patent and Trademark Office, "Requirement for Restriction," issued in connection with U.S. Appl. No. 14/188,311, dated Jan. 20, 2016, 5 pages.

United States Patent and Trademark Office, "Non-Final Office Action," issued in connection with U.S. Appl. No. 14/188,311, dated Apr. 22, 2016, 42 pages.

United States Patent and Trademark Office, "Final Office Action," issued in connection with U.S. Appl. No. 14/188,311, dated Feb. 15, 2017, 23 pages.

United States Patent and Trademark Office, "Non-Final Office Action," issued in connection with U.S. Appl. No. 14/188,311, dated Aug. 29, 2017, 22 pages.

United States Patent and Trademark Office, "Notice of Allowance," issued in connection with U.S. Appl. No. 14/188,311, dated Mar. 28, 2018, 28 pages.

* cited by examiner

CLINICAL CASE CREATION AND ROUTING AUTOMATION

FIELD OF DISCLOSURE

The present disclosure relates to data processing, and more particularly to systems, methods and computer program products for clinical case creation and routing automation.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

Healthcare entities such as hospitals, clinics, or clinical groups often employ local information systems to store and manage patient information. If a first healthcare entity having a first local information system refers a patient to a second healthcare entity having a second local information system, personnel at the first healthcare entity typically manually retrieves patient information from the first information system and stores the patient information on a storage device such as a compact disk (CD). The personnel then transport the storage device to the second healthcare entity, which employs personnel to upload the patient information from the storage device onto the second information system. Transmitting information via CD, fax, virtual private network (VPN), etc., is insufficient and unreliable for consultation, rapid diagnosis, computer-aided processing, etc.

BRIEF DESCRIPTION

Certain examples provide a cloud-based medical image and document exchange infrastructure apparatus including an instruction processor to execute an instruction to process data according to one or more defined rules, wherein the instruction is associated with a state, the state including at least active and inactive. The example apparatus also includes a gateway to at least: receive incoming data related to an imaging study; monitor the incoming data to compare the incoming data to one or more active instructions; and, when an active instruction applies to the incoming data, execute the active instruction with respect to the corresponding imaging study.

Certain examples provide a computer-readable storage medium including instructions. The instructions, when executed, cause at least one processor to at least: receive incoming data related to an imaging study; monitor the incoming data to compare the incoming data to one or more active instructions, each instruction to process data according to one or more defined rules, each instruction associated with a state including at least active and inactive; and, when an active instruction applies to the incoming data, execute the active instruction with respect to the corresponding imaging study.

Certain examples provide a computer-implemented method including receiving, by executing an instruction using at least one processor, incoming data related to an imaging study. The example method includes monitoring, by executing an instruction using the at least one processor, the incoming data to compare the incoming data to one or more active instructions, each instruction to process data according to one or more defined rules, each instruction associated with a state including at least active and inactive. The example method includes, when an active instruction applies to the incoming data, executing the active instruction using the at least one processor with respect to the corresponding imaging study.

BRIEF DESCRIPTION OF THE DRAWINGS

The features and technical aspects of the system and method disclosed herein will become apparent in the following Detailed Description in conjunction with the drawings in which reference numerals indicate identical or functionally similar elements.

Figure 1:
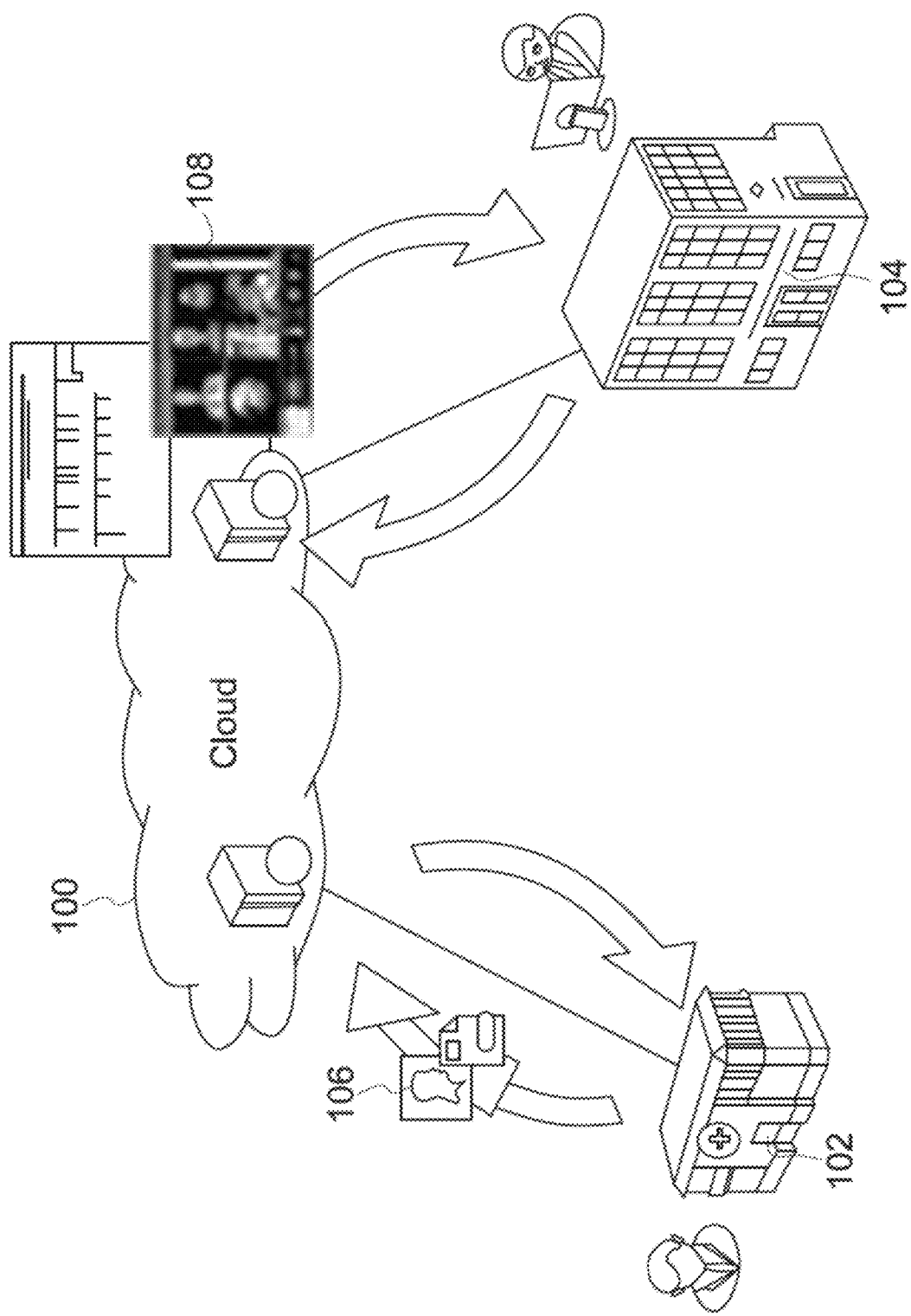
FIG. 1 illustrates an example cloud-based clinical information system employed by a first entity to share information with a second entity.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings. The figures are not scale. Wherever possible, the same reference numbers will be used throughout the drawings and accompanying written description to refer to the same or like parts.

DETAILED DESCRIPTION

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

In addition, it should be understood that references to "one embodiment" or "an embodiment" of the present disclosure are not intended to be interpreted as excluding the existence of additional embodiments that also incorporate the recited features.

I. Overview

Aspects disclosed and described herein provide improved automation of case creation and routing. Certain examples provide a cloud-based system and associated methods to manage image and/or other patient files produced by imaging devices such as computed tomography (CT) scanners, magnetic resonance imaging (MRI) devices, ultrasound machines, etc. The cloud-based system provides data structures to store, share, and analyze patient data (e.g., images, lab results, history information, etc.), for example. In certain examples, image and/or other data sharing can be facilitated between users of the cloud-based system. In certain examples, sharing can be facilitated between a first user of the cloud-based system and a second user who is not using the cloud-based system. In certain examples, users are part of the same healthcare environment. In other examples, users belong to different healthcare environments. Thus, clinicians at distant institutions can remotely consult with respect to an image exam, for example.

In certain examples, patient DICOM images and related non-DICOM medical data (e.g., results, reports, pictures, videos, etc.) can be queried and retrieved and presented in context to help a clinician to co-relate images to results to arrive at a diagnosis and/or treatment decision. Patient data can be aggregated from a plurality of disconnected files, shared, and stored in a non-DICOM format. Rather than being tied to a specific workstation or device or need multiple viewers to view all the disparate file formats, the centralized storage allows secure, reliable storage, retrieval, and review through accepted protocols (e.g., HL7, IHE-XDS, etc.).

II. Example Cloud-Based Clinical Information Systems and Methods of Use

Cloud-based clinical information systems and methods of use are disclosed herein. An example cloud-based clinical information system described herein enables healthcare entities (e.g., patients, clinicians, sites, groups, communities, and/or other entities) to share information via web-based applications, cloud storage and cloud services. For example, the cloud-based clinical information system may enable a first clinician to securely upload information into the cloud-based clinical information system to allow a second clinician to view and/or download the information via a web application. Thus, for example, the first clinician may upload an x-ray image into the cloud-based clinical information system, and the second clinician may view the x-ray image via a web browser and/or download the x-ray image onto a local information system employed by the second clinician.

In some examples, a first entity may register with the cloud-based clinical information system to acquire credentials and/or access the cloud-based clinical information system. To share information with a second entity and/or gain other enrollment privileges (e.g., access to local information systems), the first entity enrolls with the second entity. In some examples, the example cloud-based clinical information system segregates registration from enrollment. For example, a clinician may be registered with the cloud-based clinical information system and enrolled with a first hospital and a second hospital. If the clinician no longer chooses to be enrolled with the second hospital, enrollment of the clinician with the second hospital can be removed or revoked without the clinician losing access to the cloud-based clinical information system and/or enrollment privileges established between the clinician and the first hospital.

In some examples, business agreements between entities are initiated and/or managed via the cloud-based clinical information system. For example, if the first entity is unaffiliated with the second entity (e.g., no legal or business agreement exists between the first entity and the second entity) when the first entity enrolls with the second entity, the cloud-based clinical information system provides the first entity with a business agreement and/or terms of use that the first entity executes prior to being enrolled with the second entity. The business agreement and/or the terms of use may be generated by the second entity and stored in the cloud-based clinical information system. In some examples, based on the agreement and/or the terms of use, the cloud-based clinical information system generates rules that govern what information the first entity may access from the second entity and/or how information from the second entity may be shared by the first entity with other entities and/or other rules.

In some examples, the cloud-based clinical information system may employ a hierarchal organizational scheme based on entity types to facilitate referral network growth, business agreement management, and regulatory and privacy compliance. Example entity types include patients, clinicians, groups, sites, integrated delivery networks, communities and/or other entity types. A user, which may be an entity or an administrator of an entity, may register as a given entity type within the hierarchal organizational scheme to be provided with predetermined rights and/or restrictions related to sending information and/or receiving information via the cloud-based clinical information system. For example, a user registered as a patient may receive or share any patient information of the user while being prevented from accessing any other patients' information. In some examples, a user may be registered as two types of entities. For example, a healthcare professional may be registered as a patient and a clinician.

In some examples, the cloud-based clinical information system includes an edge device located at healthcare facility (e.g., a hospital). The edge device may communicate with a protocol employed by the local information system(s) to function as a gateway or mediator between the local information system(s) and the cloud-based clinical information system. In some examples, the edge device is used to automatically generate patient and/or exam records in the local information system(s) and attach patient information to the patient and/or exam records when patient information is sent to an entity associated with the healthcare facility via the cloud-based clinical information system.

In some examples, the cloud-based clinical information system generates user interfaces that enable users to interact with the cloud-based clinical information system and/or communicate with other users employing the cloud-based clinical information system. An example user interface described herein enables a user to generate messages, receive messages, create cases (e.g., patient orders), share information, receive information, view information, and/or perform other actions via the cloud-based clinical information system.

FIG. 1 illustrates an example cloud-based clinical information system 100 disclosed herein. In the illustrated example, the cloud-based clinical information system 100 is employed by a first entity 102 and a second entity 104. Example entity types include a community, an integrated delivery network (IDN), a site, a group, a clinician, and a patient and/or other entities.

In the illustrated example, the first entity 102 employs the example cloud-based clinical information system 100 to facilitate a patient referral. Although the following example is described in conjunction with a patient referral (e.g., a trauma transfer), the cloud-based information system 100 may be used to share information to acquire a second opinion, conduct a medical analysis (e.g., a specialist located in a first location may review and analyze a medical image captured at a second location), facilitate care of a patient that is treated in a plurality of medical facilities, and/or in other situations and/or for other purposes.

In the illustrated example, the first entity 102 may be a medical clinic that provides care to a patient. The first entity 102 generates patient information (e.g., contact information, medical reports, medical images, and/or any other type of patient information) associated with the patient and stores the patient information in a first local information system (e.g., PACS/RIS and/or any other local information system). To refer the patient to the second entity 104, the first entity posts or uploads an order 106, which includes relevant portions of the patient information, to the cloud-based clinical information system 100 and specifies that the patient is to be referred to the second entity. For example, the first entity 102 may use a user interface (FIGS. 9-11) generated via the cloud-based clinical information system 100 to upload the order 106 via the internet from the first local information system to the cloud-based clinical information system 100 and direct the cloud-based information system 100 notify the second entity 104 of the referral and/or enable the second entity 104 to access the order 106. In some examples, the cloud-based clinical information system 100 generates a message including a secure link to the order 106 and emails the message to the second entity 104. The second entity 104 may then view the order 106 through a web browser 108 via the cloud-based clinical information system 100, accept and/or reject the referral, and/or download the order 106 including the patient information into a second local information system (e.g., PACS/RIS) of the second entity 104. As described in greater detail below, the cloud-based-based clinical information system 100 manages business agreements between entities to enable unaffiliated entities to share information, thereby facilitating referral network growth.

Figure 2:
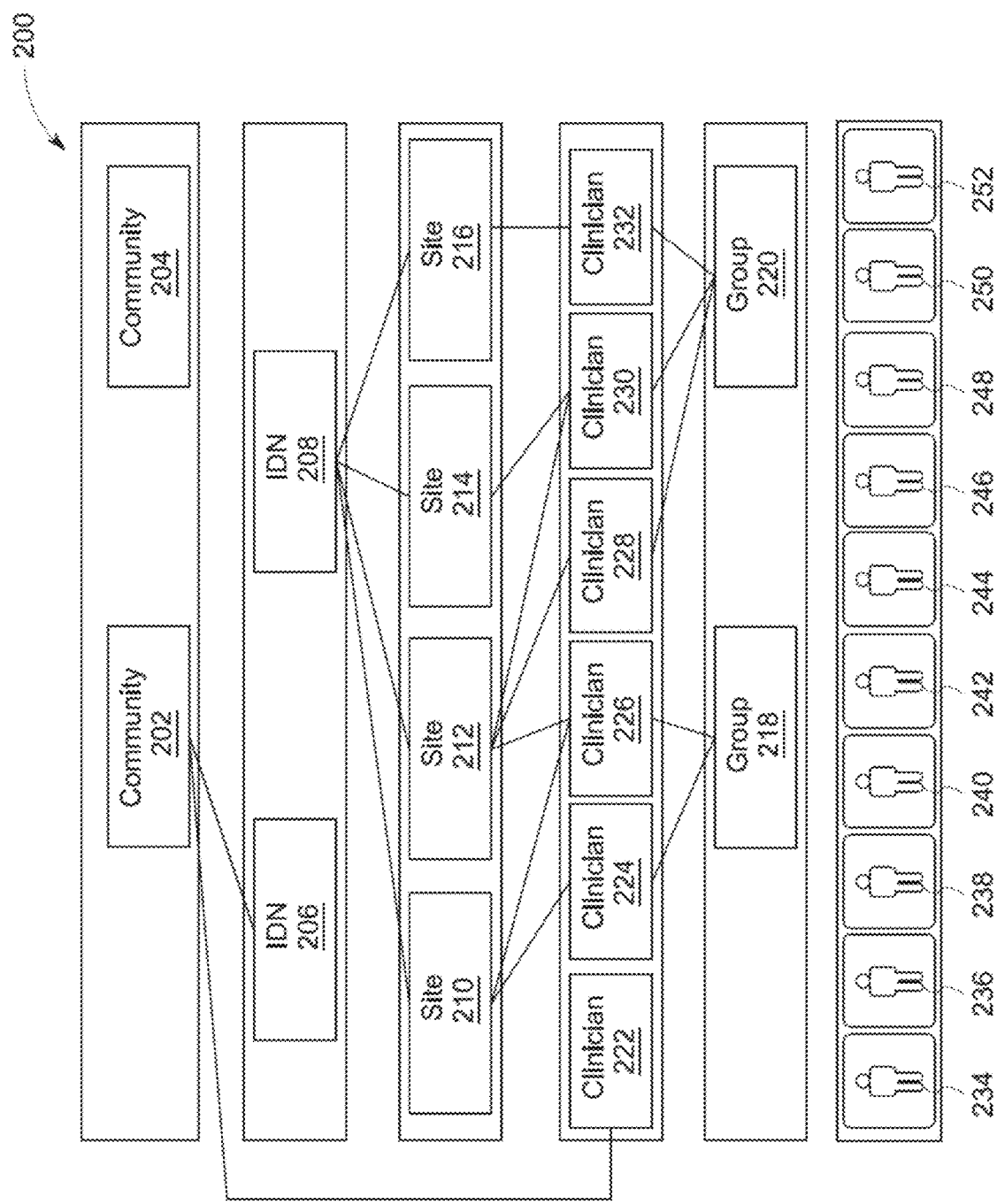
FIG. 2 is a block diagram illustrating an example hierarchal organizational system employed by the example cloud-based clinical information system of FIG. 1.

FIG. 2 illustrates an example hierarchal organization scheme 200 disclosed herein. In some examples, credentials are assigned and/or rules for accessing (e.g., viewing, receiving, downloading, etc.) information and/or sharing (e.g., uploading, sending, etc.) information via the cloud-based clinical information system 100 is governed and/or determined by the cloud-based information system 100 according to the hierarchal organization scheme 200. In the illustrated example, the hierarchal organizational scheme 200 is organized based on entity types. In the illustrated example, the entity types include communities 202, 204, IDNs 206, 208, sites 210, 212, 214, 216, groups 218, 220, clinicians 222, 224, 226, 228, 230, 232, 234, and patients 234, 236, 238, 240, 242, 244, 246, 248, 250, 252. Other examples include other entity types.

In some examples, the communities 202, 204 are legal entities. In some examples, the communities 202, 204 are defined by subject matter (e.g., medical practice type, research area and/or any other subject matter) and/or geographic location. For example, the community 202 may be a plurality of individuals, hospitals, research facilities, etc. cooperating to form a research collaboration. The IDNs 206, 208 may be a plurality of facilities and/or providers that provide a continuum of care to a market or geographic area. For example, the IDN 206 may be a plurality of medical facilities having business and/or legal relationships. The sites 210, 212, 214, 216 are medical facilities such as a hospitals, imaging centers and/or any other type of medical facility. The groups 218, 220 are a plurality of individuals having a legal-based or interest-based relationship. For example, the group 218 may be a limited liability corporation, and the group 220 may be composed of a plurality of clinicians. Clinicians 222, 224, 226, 228, 230, 232, 234 are healthcare professionals such as physicians, technicians, administrative professionals (e.g., file room clerks, scheduling administrators, reporting administrators, and/or any other administrative professionals), nurses, students, researchers, and/or any other healthcare professionals. In some examples, the clinicians 222, 224, 226, 228, 230, 232, 234 are employed by one or more of the sites 210, 212, 214, 216 and/or the groups 218, 220. The patients 234, 236, 238, 240, 242, 244, 246, 248, 250, 252 are individuals who will be or have been under the care of one or more of the clinicians 222, 224, 226, 228, 230, 232, 234.

In the illustrated example of FIG. 1, credentials and/or rules for accessing and sharing information via the cloud-based clinical information system 100 are assigned and/or governed based on the entity types. Example rules for accessing and sharing information via the cloud-based clinical information system 100 include rules related to regulatory compliance and privacy such as, for example, rules to comply with the Health Insurance Portability and Accountability Act (HIPAA). For example, one of the patients 234, 236, 238, 240, 242, 244, 246, 248, 250, 252 may access his/her patient information from any entity in communication with the cloud-based clinical information system 100 and share his/her patient information with any entity in communication with the cloud-based clinical information system 100. However, the cloud-based clinical information system 100 prohibits or prevents the patients 234, 236, 238, 240, 242, 244, 246, 248, 250, 252 from viewing, receiving or sharing other patients' information. In some examples, the cloud-based clinical information system 100 enables the clinicians 222, 224, 226, 228, 230, 232, 234 to view, receive and/or share information related to any of the patients 234, 236, 238, 240, 242, 244, 246, 248, 250, 252 which are under the clinicians' care. However, the cloud-based clinical information system 100 may prevent one of the clinicians 222, 224, 226, 228, 230, 232, 234 from viewing and/or sharing information related to one of the patients 234, 236, 238, 240, 242, 244, 246, 248, 250, 252 not under the clinicians' care.

In some examples, one entity is a member of one or more other entities. For example, as illustrated in FIG. 2, the clinician 232 is a member of the group 220 and the site 216. Thus, the clinician 232 may access and/or share information that is accessible to the group 220 and the site 216 and associated with the clinician 232 via the cloud-based clinical information system 100. For example, the clinician 232 may be employed by both the group 220 and the site 216, and the clinician 232 may use the cloud-based clinical information system 100 to access and/or share information related to patients under the care of the clinician 232 at either of the group 220 and the site 216 even if, for example, the group 220 and the site 216 are not affiliated with each other. As described in greater detail below, a first entity (e.g., the clinician 222) may become a member of second entity (e.g., IDN 206) by enrolling in the second entity via the cloud-based clinical information system.

Figure 3:
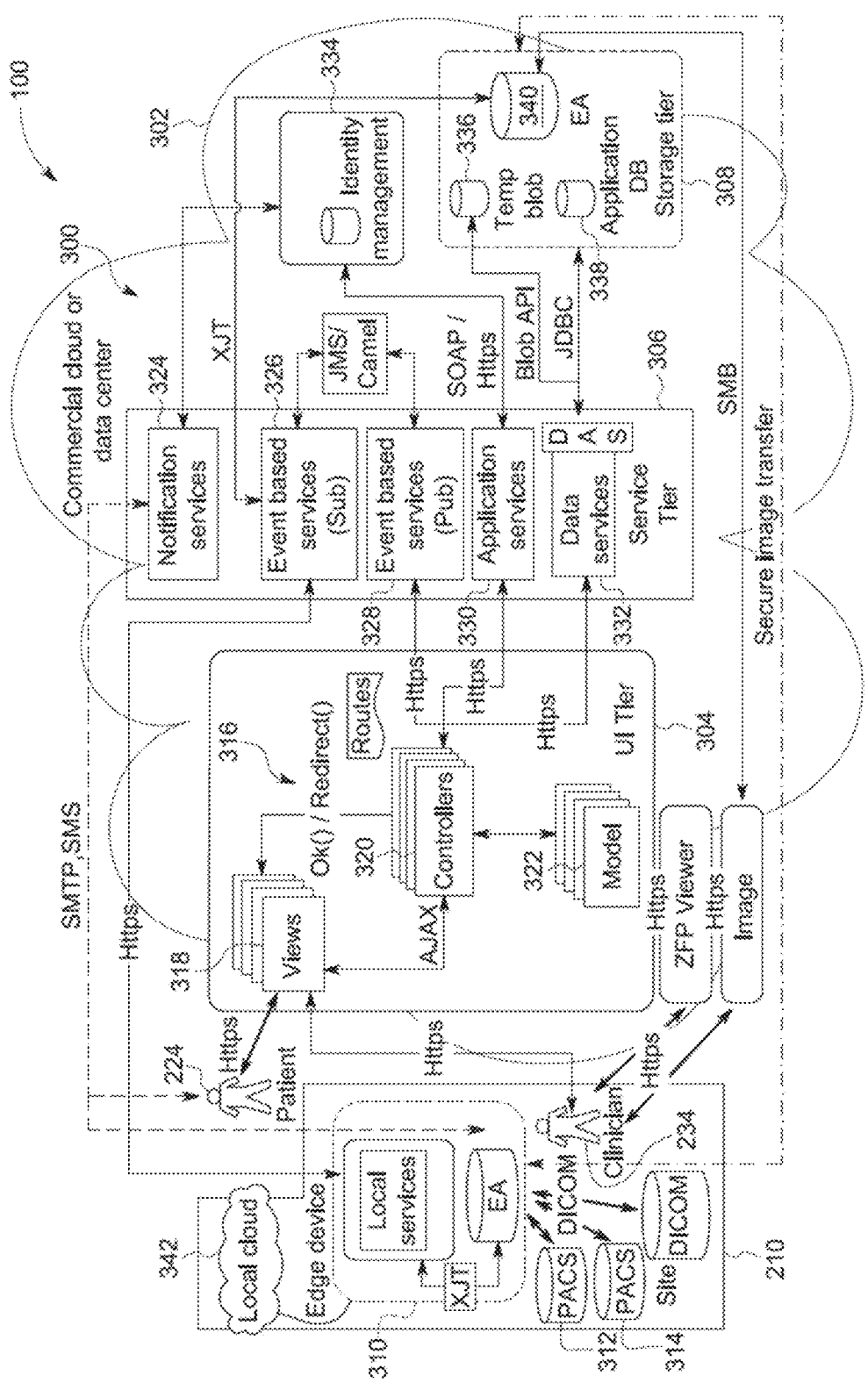
FIG. 3 illustrates an example architecture that may be used to implement the example cloud-based clinical information system of FIG. 1.

FIG. 3 illustrates an example architecture 300 to implement the example cloud-based clinical information system 100 of FIG. 1. In the illustrated example, the cloud-based clinical information system 100 includes a cloud system 302 ("cloud") having a web/user interface tier 304, a service tier 306 and a storage tier 308. In the illustrated example, the clinician 234 is located at the site 210. An example edge device 310 is located at the site 234 and facilitates communication between the cloud 302 and local information systems 312, 314 employed by the site 210. For example, the edge device 310 may communicate via DICOM and/or HL7 protocols with the local information systems 312, 314 to generate patient and/or exam records in the local information systems 312, 314, retrieve information from the local information system 312, 314 and upload the information into the cloud 300, store information in the local information systems 312, 314, and/or perform other actions. In some examples, the local information systems 312, 314 include picture archiving and communication systems (PACS), electronic health records (EMR) systems, radiology information systems (RIS) and/or other types of local information systems.

In some examples, the web/user interface tier 304 builds a user experience via model-view-controller architecture 316 including views 318, controllers 320 and models 322. For example, the views 318 request information from the models 322 to generate user interfaces that enable the clinician 234 and/or the patient 224 to view information stored in the cloud 302 via the storage tier 308. In some examples, views 318 generate zero footprint viewers that enable the clinician 234 and/or the patient 224 to view information such as medical images using a web browser. In some examples, the views 318 generate user interfaces that enable the clinician 234 and/or the patient 224 to upload information onto the cloud 302, download information from the cloud 302 onto one or more of the local information systems 312, 314 and/or perform other actions. The example models 322 include underlying data structures that include and/or organize information used by the views 318 to populate the user interfaces. The example controllers 320 request data from the service tier 306, update the models 322 and/or information employed by the models 322 and instruct the views 318 to adjust or change a presentation (e.g., change a screen, scroll, and/or any other adjustment or change to a presentation) provided via the user interfaces.

The example service tier 306 includes notification services 324, event based services 326, 328 employing a publishing-subscribing messaging model, application or web services 330, data services 332, identity management services 334 and/or other services. The example user interface tier 304 The example storage tier 308 includes a plurality of storage devices 336, 338, 340 (e.g., databases, blobs, image management and storage devices, and/or any other storage devices). The example notification services 324 generate and communicate (e.g., via email, text message and/or any other way) notifications to users of the example cloud-based clinical information system 100. For example, if the clinician 234 is referred a case via the cloud-based clinical information system 100, the notification services 324 may generate and communicate a text message to a phone associated with the clinician 234 that indicates that information related to the case is accessible via the cloud-based clinical information system 100. The example application services 330 and the identity management services 334 cooperate to verify user credentials and/or manage rules related to receiving and sharing information via the cloud-based clinical information system 100 based on the credentials. For example, if the user is a patient, the application services 330 and/or the identity management services 334 may prevent the user from accessing information related to other patients. In some examples, the user interface tier 304 and the service tier 306 interact asynchronously. For example, the controllers 320 may communicate a request for information stored in an image management and storage device (e.g., storage device 340) via the data services 332, and the request may be input into a worklist or queue of the service tier 306. Other architectures are used in other examples.

As described in conjunction with FIG. 1 above, the example cloud-based clinical information system 100 may be used to share information between entities such as the patient 224 and the site 210. For example, the clinician 234 may prepare a medical report and upload the medical report onto the cloud 302 via a user interface generated by the example user interface tier 304. The example notification services 324 may notify the patient 224 that the report is accessible via the cloud-based clinical information system 100, and the patient may use a web browser to view the report via a zero footprint viewer generated by the views 318.

In some examples, the cloud-based clinical information system 100 is a hybrid cloud system including the cloud 302 and a local cloud 342. For example, the cloud-based clinical information system 100 may enable the site 210 to share information with unaffiliated entities via the cloud 302 and share information with affiliated entities via the local cloud 342 and/or the cloud 302. In some examples, the cloud 302 and the local cloud 342 are hierarchal. For example, the cloud-based clinical information system 100 may allocate or divide tasks, information, etc. between the cloud 302 and the local cloud 342 based on resources and/or data availability, confidentiality, expertise, content of information, a type of clinical case associated with the information, a source of the information, a destination of the information, and/or or other factors or characteristics. Some example cloud-based clinical information systems do not employ the local cloud 342.

The example local cloud 342 of FIG. 3 is implemented by the example edge device 310. In some examples, the edge device 310 employs a substantially similar architecture to the example architecture 300 of the cloud 302 of FIG. 3 to implement the example local cloud 342. Thus, the example local cloud 342 may generate user interfaces, perform notification services, manage and store data, and/or perform other actions and/or services that can be used by entities affiliated with the site 210. In some examples, the local cloud 342 functions as a backup to the cloud 302 with respect to information related to the site 210 and/or function as a backup to the local information systems 312, 314. In some examples, the local cloud 342 employs a different architecture than the architecture 300 of the cloud 302 and/or performs different services than the cloud 302.

In some examples, the edge device uploads information from the local information systems 312, 314 to the local cloud 342 and/or the cloud 302. In some examples, the edge device 310 analyzes information generated by, stored in and/or used by the local information systems 312, 314 and determines which information is to be uploaded onto the cloud 302 and/or which information is to be uploaded onto the local cloud 342. In some examples, the edge device 310 determines that information is to be uploaded in only one of the cloud 302 or the local cloud 342. In some examples, the edge device 310 determines that information is to be uploaded to both the cloud 302 and the local cloud 342. In some examples, information from the local information systems 312, 314 and/or from the affiliated entities is routed through the example edge device 310 to enable the edge device to analyze the information to determine if the information is to be uploaded onto the cloud 302 and/or the local cloud 342.

In some examples, information is uploaded onto the local cloud 342 based a type of the information and/or content of the information. For example, the edge device 310 may monitor information stored in and/or used by the local information systems 312, 314 and/or communicated between the site 210 and affiliated entity(-ies) to determine types and/or content of information and, based on the types and/or content of information, upload the information onto the cloud 302 and/or local cloud 342. For example, information related to clinical care of patients may be uploaded and stored in the local cloud 342. In some examples, the information is stored in the local cloud 342 temporarily. For example, if a patient is undergoing a surgical procedure at the site 210, information related to the surgical procedure and the patient may be stored in the local cloud 342 and accessible via the local cloud 342 throughout the surgical procedure. Following the surgical procedure, the information may be removed from the local cloud 342 and/or forwarded to the cloud 302. In some examples, information that is to be used only by healthcare personnel at the site 210 is stored in the local cloud 342. For example, information related to internal policies of the site 210 may be stored in the local cloud 342. In other examples, information is uploaded onto the local cloud 342 for other reasons and/or based on other factors and/or determinations.

In some examples, information is uploaded onto the cloud 302 based on a type of information. For example, information to be accumulated for clinical analysis (e.g., as part of a long-term study) may be uploaded onto the cloud 302. In some example, information to be accessible to entities other than the site 210 is uploaded onto the cloud 302 by the edge device 310. For example, if the clinician 234 refers a patient to another entity via the cloud-based clinical information system 100, the edge device 310 retrieves information related to the patient from the local information systems 312, 314 and uploads the information to the cloud 302. In other examples, the edge device 310 uploads information to the cloud 302 for other reasons and/or based on other factors and/or determinations.

In some examples, the edge device 310 uploads information onto the cloud 302 and/or the local cloud 310 based a case type associated with the information and/or a business and/or legal relationship between a source of the information (e.g., the site 210) and a destination of the information (e.g., an affiliated entity or an unaffiliated entity). Case types include, for example, a trauma case, a specialty case (e.g., an oncology case), a second opinion case, a clearing house case, an image distribution case, a patient referral case, a foreign study management case, a remote interpretation case, a specialty treatment planning case, a review board case, a teaching case, a research exchange case and/or other case types. As described in greater detail below in conjunction with FIG. 7, the edge device 310 may determine if entities are affiliated or unaffiliated based on business and/or legal agreements uploaded, managed and/or utilized by the example cloud 302 and/or the example local cloud 342 that are used to establish credentials, access rights and/or sharing rights, and/or the privileges for the entities via the cloud-based clinical information system 100.

A trauma case arises when the clinician 234 is treating a patient in need of a higher level of trauma treatment that is not available at the site 210. The clinician 234 sends the patient to a healthcare facility with higher trauma treatment capabilities and shares information related to the patient with a clinician at the healthcare facility via the cloud-based clinical information system 100. In some examples, the information related to the trauma case is uploaded onto the local cloud 342 by the edge device 310 and not uploaded onto the cloud 302 if the healthcare facility is affiliated with the site 210 to conserve time and/or costs associated with bandwidth usage. In some examples, the edge device 210 uploads the information related to the trauma case onto the local cloud 342 and the cloud 302.

A specialty case arises when the clinician 234 is treating a patient in need of specialty treatment not available at the site 210. The clinician 234 sends the patient to another healthcare facility that provides the specialty treatment and shares information related to the specialty case to a clinician at the other healthcare facility via the hybrid cloud system. In some examples, the information is uploaded onto local cloud 342 by the edge device 310 if the healthcare facility is affiliated with the site to conserve time and/or costs associated with bandwidth usage. In some examples, the edge device 310 uploads the information related to the specialty case onto the local cloud 342 and the cloud 302.

A second opinion case arises when the clinician 234 has diagnosed a patient and would like to receive affirmation of the diagnosis from a clinician located at another healthcare facility. The clinician 234 shares information related to the second opinion case to a clinician at the other healthcare facility via the cloud-based clinical information system 100. In some examples, the information is uploaded onto local cloud 342 by the edge device 310 if the healthcare facility is affiliated with the site 210 to conserve time and/or costs associated with bandwidth usage, but the edge device 310 does not upload the information onto the cloud 302 unless instructed by the clinician 234.

A clearing house case arises when the site 210 sends information related to a plurality of cases to a clearing house entity to standardize case demographics and/or other clinical characteristic to enable ingestion of the information into the site 210. In some examples, if the clearing house entity is affiliated with the site 210, the information is shared via the cloud-based clinical information system 100, and the edge device 310 uploads the information onto the local cloud 342 and not onto the cloud 302. In some examples, the local cloud 342 performs demographic standardization of the information and enables the clinician 234 and/or other healthcare professionals to view the information via a zero footprint viewer.

An image distribution case arises when the site 210 sends information to a generic entity that will be accessed by a group of clinicians or users remotely providing case review. If the generic entity is affiliated with the site 210, the edge device 310 shares the information via the local cloud 342.

A patient referral case arises when the clinician 234 is a general practitioner and requests a specialist to review a patient case through an affiliated, disconnected network. In some examples, the edge device 310 shares information related to the patient case to the specialist via the local cloud 342 and not via the cloud 302. In some examples, the edge device 310 shares the information via the local cloud 342 and uploads the information onto the cloud 302.

A foreign study management case arises when the site 210 receives a large volume of cases involving studies that are to be managed, routed and/or classified to enable the studies to be ingested by one or more of the local information systems 312, 314. In some examples, the information is received via one or more portable storage devices (e.g., compact disks). When the information is ingested from the portable storage device(s), the edge device 310 shares the information via the local cloud 342 to conserve time and/or reduce costs associated with bandwidth usage. In some examples, the edge device 310 shares the information via the local cloud 342 and uploads the information onto the cloud 302 based on criteria such as department affiliation, traffic volume, referring source, availability of a patient portal and/or patient request, and/or other criteria.

A remote interpretation case arises when a clinician in a remote or rural geographic location requests an expert at the site 210 to interpret a patient case. If the clinician and the site 210 are unaffiliated, the clinician shares the information via the cloud 302 and not via the local cloud 342.

A specialty treatment planning case arises when a patient case involves a patient having a chronic disease that warrants planning services and a treatment plan from a specialized facility. The clinician 234 may send the patient to another healthcare facility that provides the planning services and shares information related to the specialty treatment planning case to a clinician at the other healthcare facility via the cloud-based clinical information system 100. In some examples, the information is uploaded onto local cloud 342 by the edge device 310 if the healthcare facility is affiliated with the site 210 to conserve time and/or costs associated with bandwidth usage. In some examples, the edge device 310 uploads the information related to the specialty case onto the local cloud 342 and the cloud 302.

A review board case (e.g., a tumor review board or multidisciplinary team (MDT) case) arises when the site 210 sends a patient case to a review board (e.g., a tumor review board) to enable members of the review board to review the patient case. In some examples, the review board employs an edge device to manage information traffic between the members and traffic between the review board and the site 210. In some examples, if the review board and the site are affiliated, the edge device 310 shares information related to the patient case via the local cloud 342. A teaching case arises when the site 210 shares a patient case suitable for education or instruction to an entity for repository and/or to be viewed by students or healthcare professionals. In some examples, the edge device 310 anonymizes the patient case and shares the patient case to affiliated entities via the local cloud 342 and unaffiliated entities via the cloud 302. In some examples, the edge device 310 distributes teaching cases between the cloud 302 and the local cloud 342 based on contributors of the teaching cases, students to be taught based on the teaching case, type of teaching case (e.g., modality, medical phenomena, procedure, etc.).

A research case arises when a researcher at the site 210 shares a case with a colleague prior to submission of a medical paper or article. In some examples, the edge device 310 shares the patient case to affiliated entities via the local cloud 342 and unaffiliated entities via the cloud 302.

Figure 4:
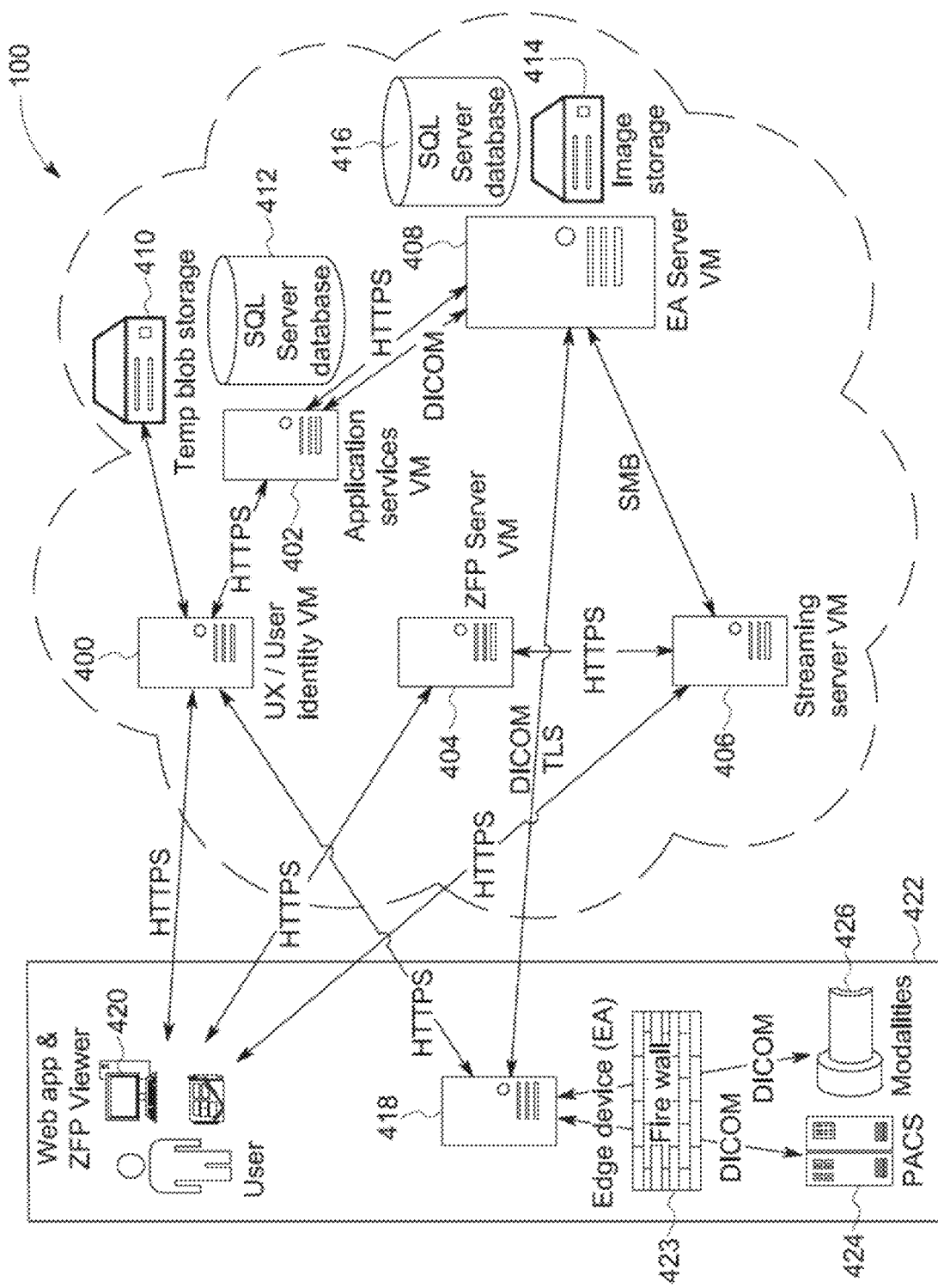
FIG. 4 illustrates an example architecture that may be used to implement the example cloud-based clinical information system of FIG. 1.

FIG. 4 illustrates an example implementation of the example cloud-based clinical information system 100 of FIG. 3. In the illustrated example, the cloud 302 includes a user experience virtual machine 400, an application services virtual machine 402, a zero footprint server virtual machine 404, a streaming server virtual machine 406, an image storage and management virtual machine 408 and a plurality of storage devices 410, 412, 414, 416 in communication with an edge device 418 and a viewer 420 (e.g., a workstation having a web browser) of a site 422 such as a hospital. In the illustrated example, a firewall 423 controls information traffic between the edge device 418 and a PACS 424 of the site 422 and between the edge device 418 and modalities 426 of the site 422.

In the illustrated example, functions of the user interface tier 304, the application services 330 and the identify management services 334 are performed via the user experience virtual machine 400. Functions of the notification services 324, the event based services 326, 328 and the data services 306 are performed via the example application services virtual machine 402. The example zero footprint virtual machine 404 is used to perform functions of the user interface tier 304 such as rendering views or presentations, populating the views, providing user tools within the views, and/or other functions. The example streaming server virtual machine 406 retrieves information from, for example, the storage device 336, 338, 340 to populate views generated by the user interface tier 304. The example image management and storage virtual machine 408 is used to manage information flow between the storage devices 336, 338, 340 and one or more of the edge device 418, the application services virtual machine 402, and the streaming server virtual machine 406.

Figure 5:
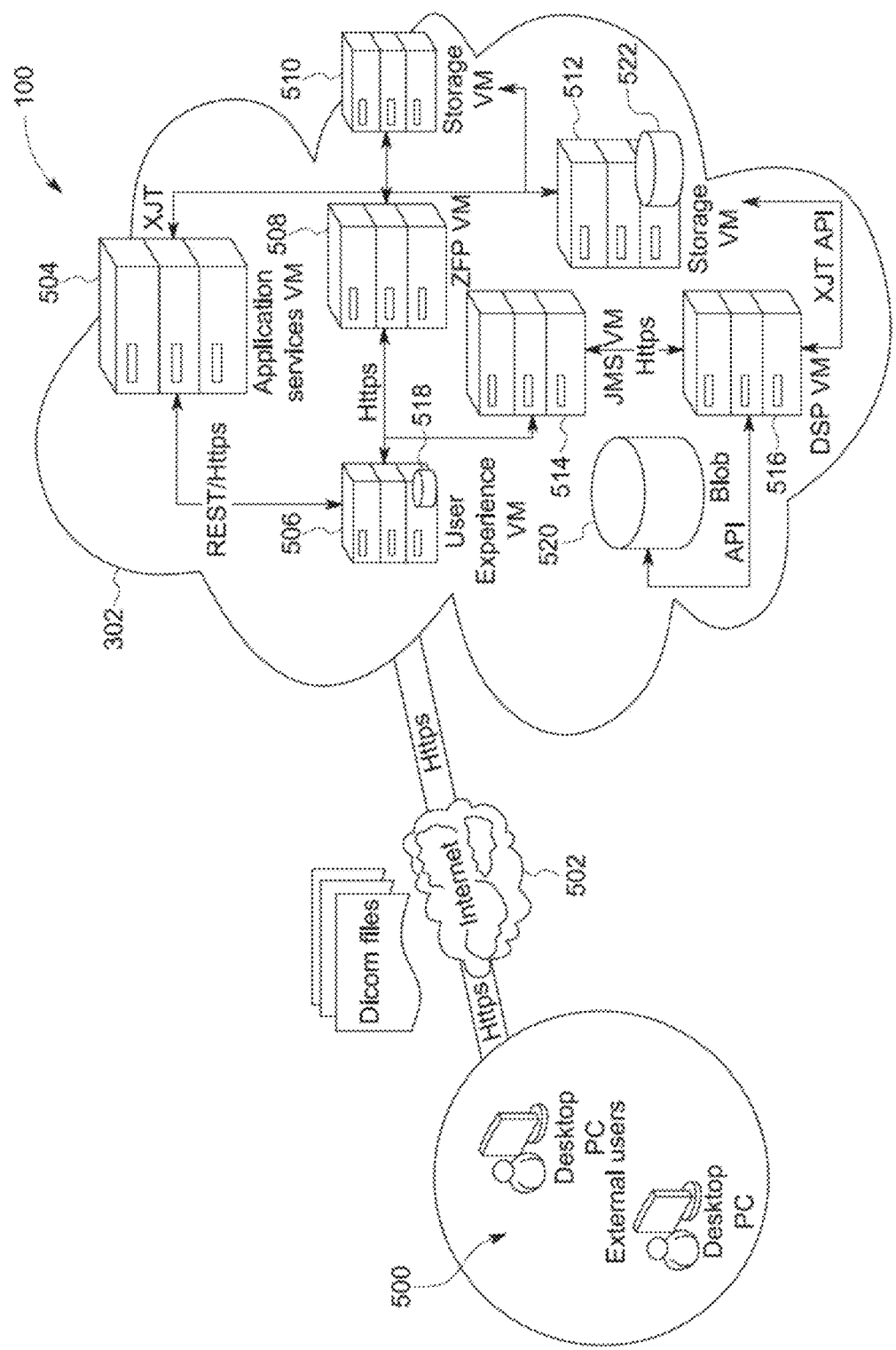
FIG. 5 illustrates an example architecture that may be used to implement the example cloud-based clinical information system of FIG. 1.

FIG. 5 illustrates another example implementation of the example cloud-based clinical information system 100. In the illustrated example, a plurality of entities 500 are in communication with the cloud 300 via the internet 502. The example cloud 300 includes an application services virtual machine 504, a user experience virtual machine 506, a zero footprint viewer virtual machine 508, information management and storage virtual machines 510, 512, a JMS virtual machine 514, a DSP virtual machine 516 and a plurality of storage devices 518, 520, 522. In some examples, functions of the example application services 330 and/or the identity management services 334 such as verifying user credentials and/or managing rules related to receiving and sharing information via the credentials are performed via the application services virtual machine 504. In some examples, functions of the user interface tier 304, the application services 330 and the identify management services 334 are performed via the user experience virtual machine 506. The example zero footprint virtual machine 508 is used to perform functions of the user interface tier 304 such as rendering views or presentations, populating the views, providing user tools within the views, and/or other functions. In some examples, functions of the notification services 324, the event based services 326, 328 and the data services 306 are performed via the example JMS virtual machine 514 and/or the DSP virtual machine 516. The example information management and storage virtual machines 510, 512 are used to manage information flow within the example cloud 302 of FIG. 5.

III. Example Case Creation and Routing Automation Systems and Associated Methods In certain examples, a cloud-based platform includes an application as associated portal to exchange images and related cases between users via the cloud-based system. For example, a local device, such as a PACS, enterprise archive, vendor neutral storage, etc., can upload DICOM studies to the cloud platform. DICOM studies can be viewed via the cloud platform using an integrated DICOM image viewer, for example. Devices can share and collaborate on cases, download images and documents (e.g., to a local PACS, etc.), manage contacts/connections, etc.

The cloud-based platform provides a scalable, secure, reliable ecosystem facilitating collaboration, device integration, user control, and data management. Patient images and other documents can be distributed between healthcare providers across geographical distances, organizations, and network boundaries. Devices and associated users can connect to (e.g., log in to) the cloud platform to share patient images and documents with other devices/users. Distribution of patient images and results is securely managed between healthcare providers across geographical distance or network boundary through a professional network. Affiliated and non-affiliated physicians can participate in a clinical community to confer on patient cases, joint access patient images and reports, and collaborate on diagnosis and treatment plans, for example. Certain examples facilitate case exchange, multidisciplinary team coordination, image access, etc.

For example, case creation can be automated with the cloud-based server under case exchange. Rules and/or other instructions can be defined to drive automated case creation and routing. For example, an instruction or rule can be set up to identify an incoming image of a certain type (e.g., a magnetic resonance image of a brain, etc.) with a certain associated clinician (e.g., reporting physician is Dr. Smith, etc.). When such an image is identified, the example rule instructs that associated metadata (e.g., in a DICOM header of the image, etc.) is processed to create a case on the cloud from the image. According to the example rule/instruction, the automatically created case is forwarded to the associated clinician (e.g., sent to Dr. Smith, etc.).

In certain examples, when a case has already been created, actions can be automatically prescribed with respect to the existing case. For example, an instruction can be created to route incoming information and/or otherwise take action on an existing case (e.g., automatically download an image to a PACS from another organization without manual intervention, automatically forward to a user and/or group, etc.). For example, a person who is going to be out of the hospital can create an instruction to automatically forward an incoming case to another user based on certain criteria, etc.

In certain examples, data sharing can be defined as a case to be exchanged. Users desiring to share data can define rule(s) and take action on the data to be shared as part of a case to be exchanged, for example.

In certain examples, orders can be integrated into a case. For example, result orders can be automatically integrated into a case such as a case created for an x-ray of an ankle. Database information can be automated, and a study for the ankle x-ray image(s) can be integrated into the case. An order for a study can be automatically created and downloaded to a PACS from the case exchange, for example. At the click of a button and/or other selection, metadata can be read (e.g., from an image DICOM header, etc.) and supplemented with a form so that a study can be downloaded (e.g., to a PACS, etc.).

In an example, an order can be automatically created and a study downloaded with an order into a local PACS. The study can be read by a radiologist, who dictates a report of the image. When the report is dictated, the corresponding case can be updated in the cloud with results to provide a more complete picture of the study and final report in the cloud. In certain examples, an image access application can be tied in to complete the picture with the final report so that a doctor can see results for his/her patients and see all image data and reports in one place.

Thus, a cloud-based case exchange can facilitate creation of instructions to apply to incoming image studies and/or other data. In certain examples, the creator of an instruction can suspend or inactivate that instruction. Instructions define conditions regarding when to export a study. A gateway looks at the instructions to see if an instruction matches data coming from a data source (e.g., in its DICOM header, etc.). If a match is made, then the gateway executes the applicable instruction(s). Otherwise, no instruction is executed without a match.

In certain examples, instructions are presented visually in a list for selection via a graphical user interface. An instruction can be created, activated, suspended/inactivated, etc., via the graphical user interface. An organizational gateway can be selected to route case information, and an activity log can track execution of instructions. For example, the activity log can identify a matching study meeting criterion(-ia) including instructions, name(s) of instruction(s) met, case identifier, patient name, and status (e.g., failure or success including hyperlink to the case, etc.) across one or more sites, etc. The gateway checks incoming data against active (e.g., not inactivated or suspended) instructions. If conditions defined in the instruction match incoming metadata, then the gateway runs the instruction to create a case, for example. For example, the instruction can specify a particular PACS at a particular site, and the gateway checks for that PACS at that site to apply the instruction, rather than other PACS at other sites, etc.

In certain examples, routing instructions can be defined where a case is coming from and where the case is going. Cases can be routed to another system or user, automatically downloaded to a PACS and/or other local system, etc.

In certain examples, a sequence of instructions and/or other events can be reviewed with respect to a case (e.g., in a case summary section of a case record and/or other interface, for example). A first PACS can receive an image study case and route the content to another PACS, for example. Certain examples trigger the start of an MDT meeting through the case exchange, for example, and control reverts back to case exchange (e.g., to a requesting user's inbox, etc.) once the MDT meeting is complete. In certain examples, rather than single, separate transactions, a case can include an umbrella defining options for execution as well as events in chronological order.

Figure 6:
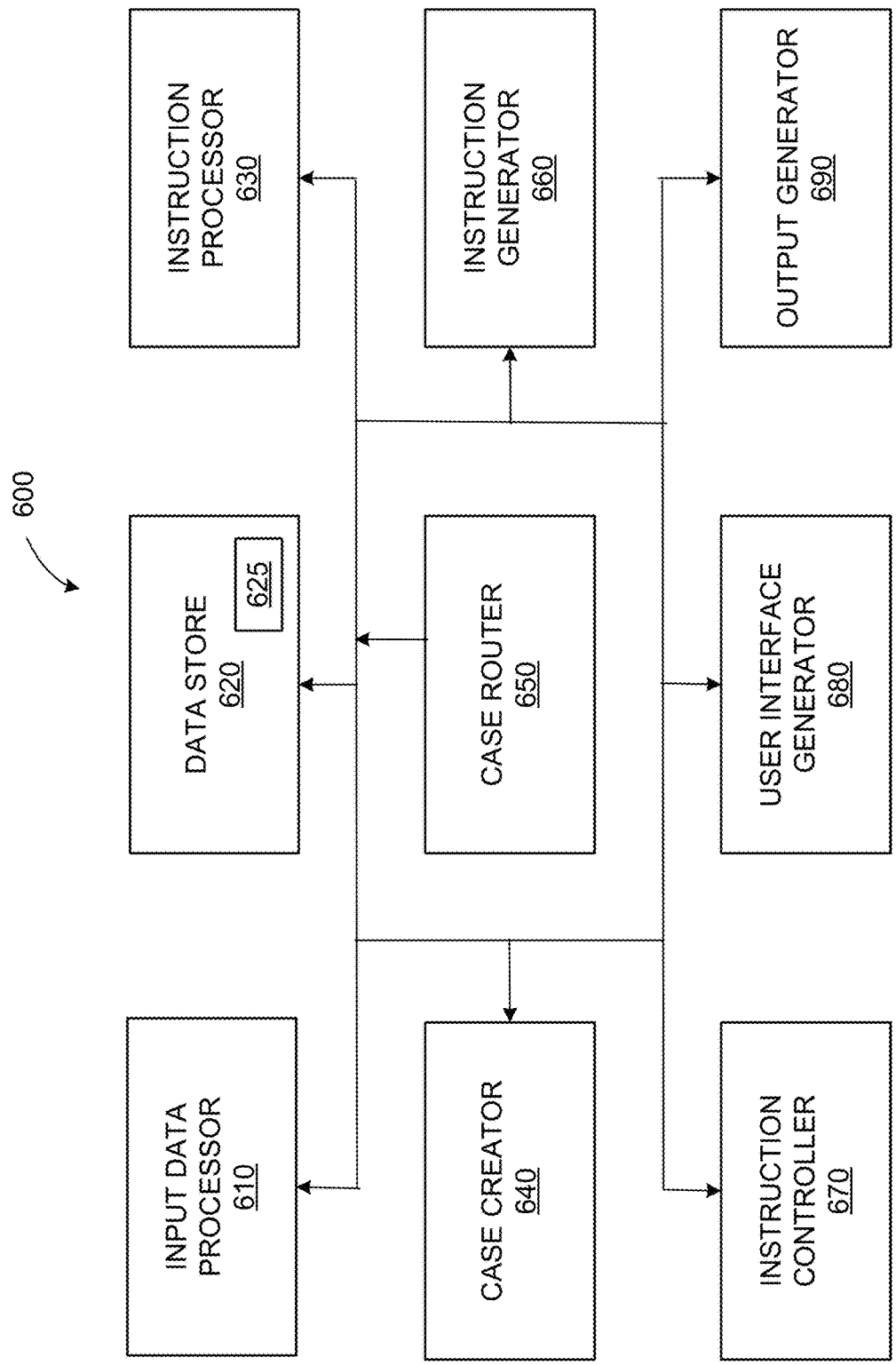
FIG. 6 shows an example clinical case creation and routing automation system.

FIG. 6 illustrates an example automated cloud-based clinical case creation and routing system 600. The example system 600 provides a cloud-based medical image and document exchange infrastructure apparatus 600, which includes an input data processor 610, a data store 620 including an instruction repository 625, an instruction processor 630, a case creator 640, a case router 650, an instruction generator 660, an instruction controller 670, a user interface generator 680, and an output generator 690.

The example system 600 receives data (e.g., image data, other patient data, etc.) at the input data processor 610, which can be connected to and/or include a gateway and/or other edge device connecting a local system to the cloud-based case creation and routing system 600. The input data processor 610 processes the incoming data to determine a type of the data, data value(s), etc., and identify whether or not a case exists associated with the data. For example, the data can include image data with a DICOM header that identifies an associated case or includes information that can be used to identify a case with which the image data is associated (e.g., patient name, other patient identifier (e.g., social security number, patient index, etc.), patient address, patient signature, etc.). The input data processor 610 can compare an identification of the data with case information stored in the data store 620 to determine whether a case exists for the data.

The input data processor 610 triggers the instruction processor 630 to evaluate instructions in the instruction repository 625 of the data store 620 to determine whether the input data satisfies any instruction. For example, the instruction processor 630 examines each instruction that is active (e.g., has an active state versus an inactive state) in the instruction repository 625 to determine whether the instruction applies to the data. Some instructions may have been inactivated or suspended, and those instructions need not be analyzed. For example, information gained by the input data processor 610 in examining the input data can be used to determine whether an active instruction or rule stored in the instruction repository 625 applies to the data. For example, if the input data is x-ray image data, the instructions can be evaluated to determine whether they apply to x-ray image data. If the input data relates to an existing case, the instructions can be evaluated to determine whether they apply to new or existing cases, for example. If the input data relates to a certain hospital or clinician, as specified in metadata in the input data file, then the instructions can be filtered by the instruction processor 630 based on the specified clinician, location, etc., for example.

One or more instructions examined by the instruction processor 630 can be selected as relevant to apply to the input data. Based on whether the instruction includes creating a case or routing for an existing case, the case creator 640 and/or the case router 650 is triggered by the instruction processor 630 and the corresponding instruction(s). The case creator 640 opens a case with respect to the input data according to the instruction and registers the case in the data store 620 so that it can later be found and retrieved, supplemented, processed, etc. The case router 650 identifies a corresponding case and routes the input data according to the instruction with respect to the existing case, for example.

In certain examples, the instruction generator 660 enables creation of instruction(s) to be stored in the data store 620 and applied to incoming data. For example, a case creation instruction can be formed by providing an instruction name, description of the instruction (e.g., rules for processor execution, etc.), identification of the instruction creator, target for the instruction (e.g., group, user name, location, etc.), privacy designation (e.g., open, private, limited collaboration, etc.), priority (e.g., low, normal, high, etc.), clinical reason (e.g., collaboration, historical patient information, multi-disciplinary team meeting, off-hour read, patient transfer, second opinion, protocol, legal request, trauma transfer, etc.), instruction duration (e.g., always, limited time period, etc.), applicability (e.g., particular location(s), particular department(s), particular role(s), particular user(s), particular exam type(s), particular application service(s), etc.), filter conditions (e.g., no condition, custom condition(s) (e.g., modality, referring physician name, study description, performing physician name, patient age, etc.), etc. For example, a case routing instruction can be formed by providing an instruction name, description of the instruction (e.g., rules for processor execution, etc.), intended recipient of the instruction (e.g., a creating user him-/herself, a colleague, a subordinate, etc.), case details (e.g., cases shared from a name or group, etc.), instruction duration (e.g., always, limited time period, etc.), filter conditions (e.g., no condition, custom condition(s) (e.g., modality, referring physician name, study description, performing physician name, patient age, etc.), routing information (e.g., routing to another person or group, etc.), download instructions (e.g., reconcile and download to PACS, direct download to PACS, etc.), etc.

The instruction is then generated by the instruction generator 660 provided for selection by the instruction controller 670 via a user interface generated by the user interface generator 680. The instruction controller 670 can control to whom the instruction(s) are made available, whether the state of the instruction is active or inactive/suspended, etc. The user interface generator 680 facilitates display and selection of instructions (e.g., for a user, location, organization, function, etc.), and the output generator 690 provides results of instruction execution such as case creation, case routing to a PACS, other data storage, other system, etc., and the like. The user interface generator 680 can also display an activity log showing a history of usage, modification, activation/deactivation, etc., of available instructions, as captured by the instruction controller 670, for example.

In certain examples, instructions are associated with a particular gateway, so a user first selects an available gateway for connection to the cloud-based system 600, and available instructions then appear for the selected gateway. The user can then select active instruction(s) and/or active instruction(s) are then automatically applied to incoming data, for example.

In certain examples, once a case has been created and/or routed, the case can be opened for review, editing (e.g., to add to a case, etc.), collaboration (e.g., electronic conversation, multi-disciplinary team meeting (e.g., tumor board, etc.), etc.), processing, presentation, export, etc. Results can be saved (e.g., locally and/or remotely), exported, routed to another application and/or system, etc.

Figure 7A:
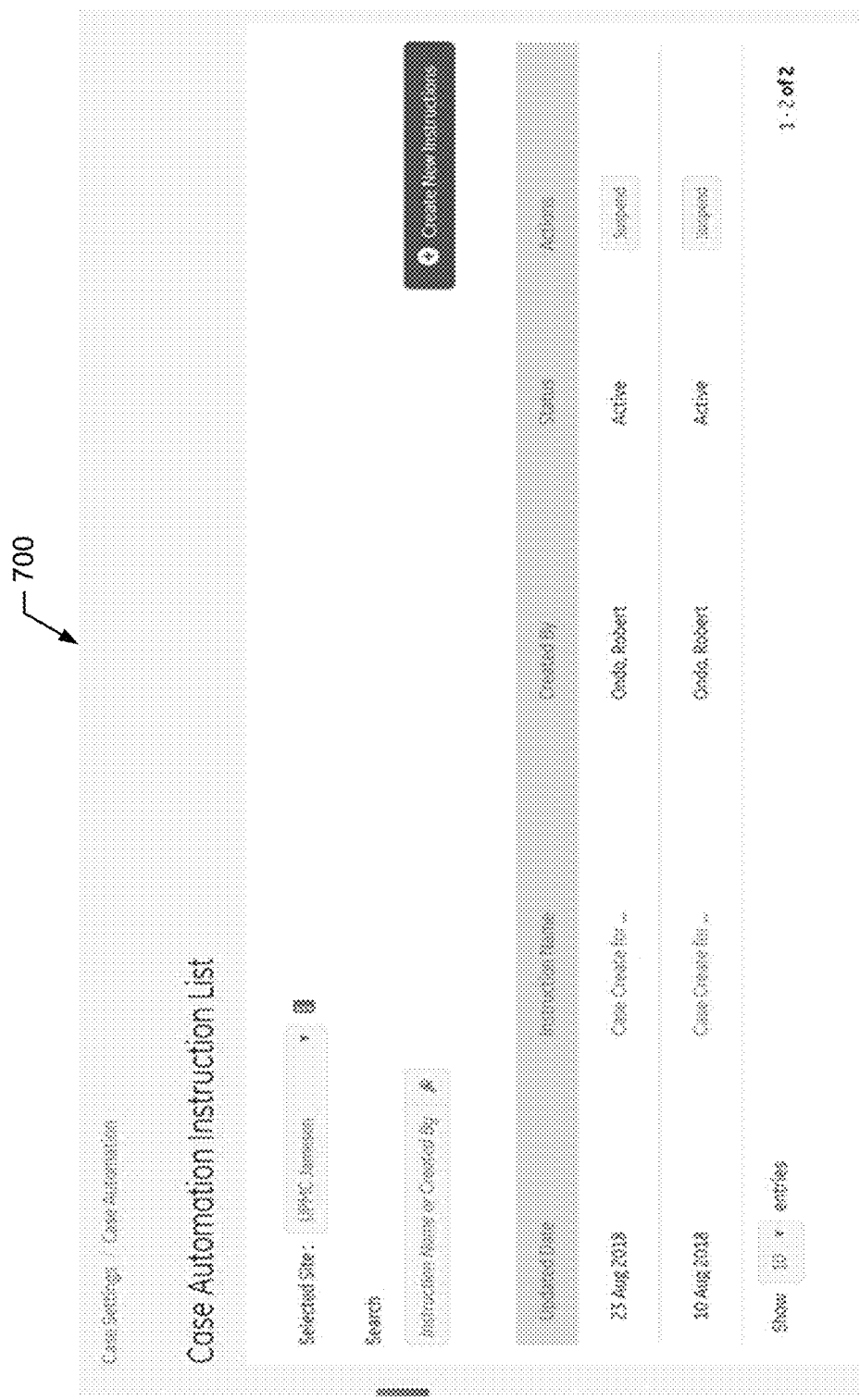
FIGS. 7A-7B show example graphical user interfaces associated with the system of FIG. 6.
Figure 7B:
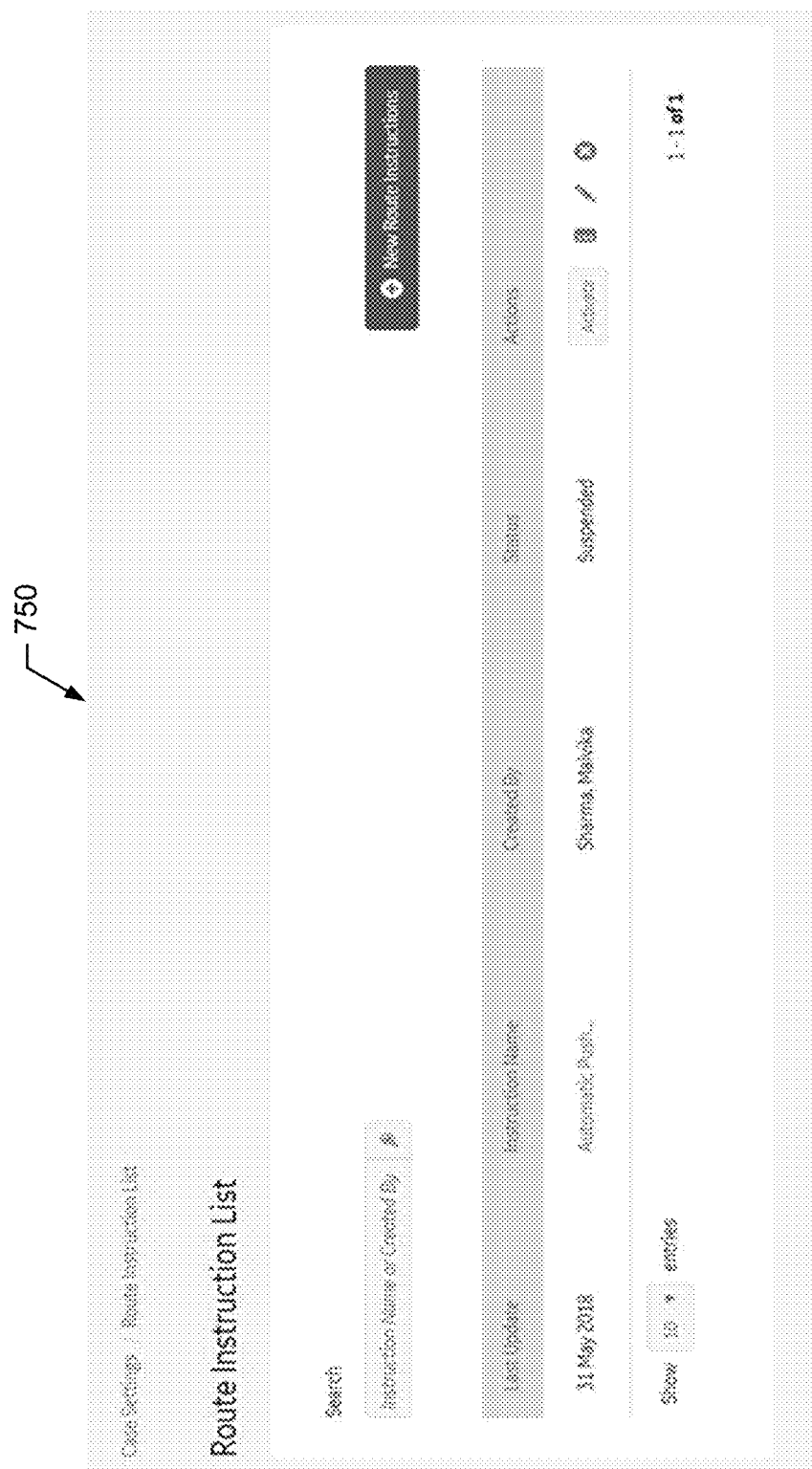

FIG. 7A depicts an example user interface 700 generated by the user interface generator 680 to display case creation instructions for selection. FIG. 7B shows an example user interface 750 generated by the user interface generator 680 to display case routing instructions for selection.

Figure 8:
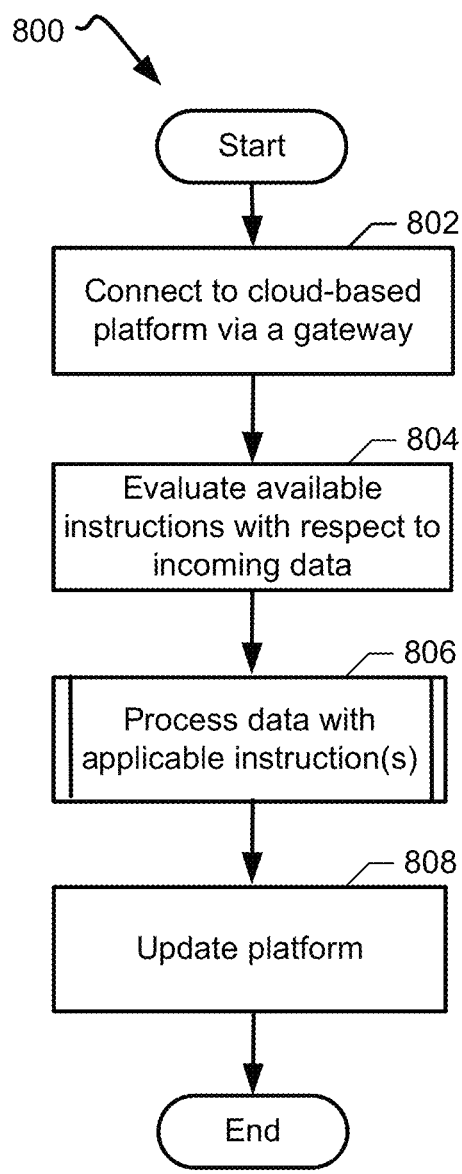
FIGS. 8-10 illustrate flow diagrams for example methods of case creation and routing automation.
Figure 9:
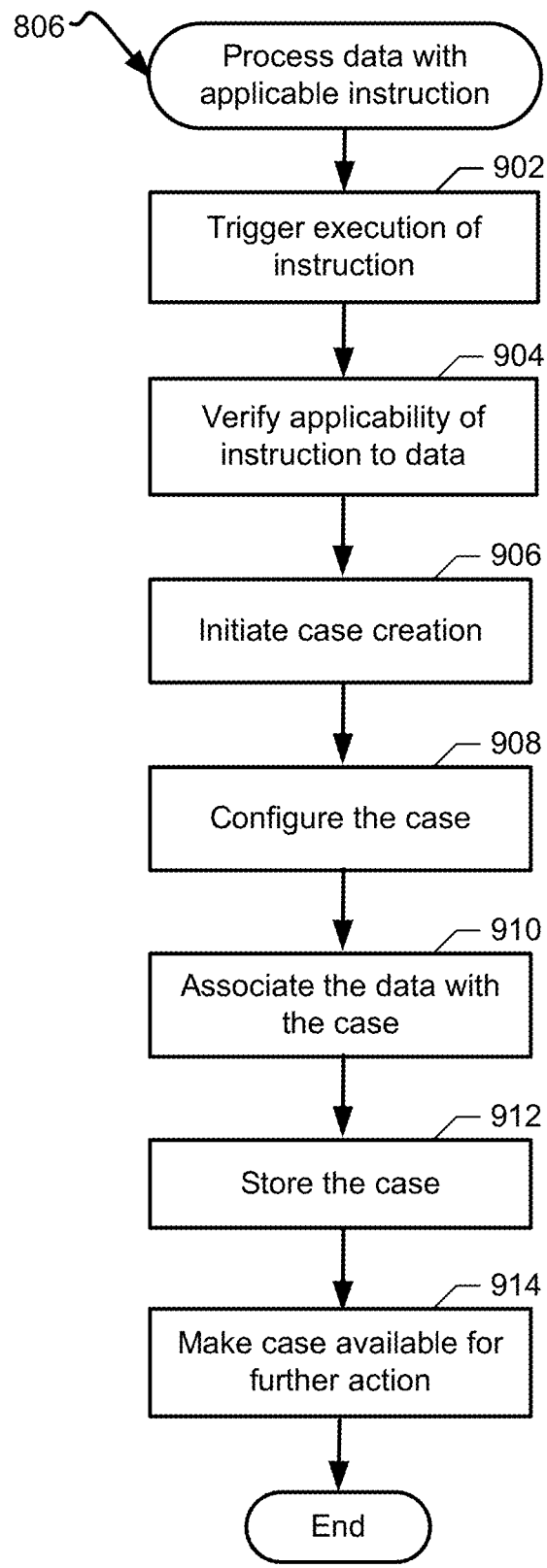
Figure 10:
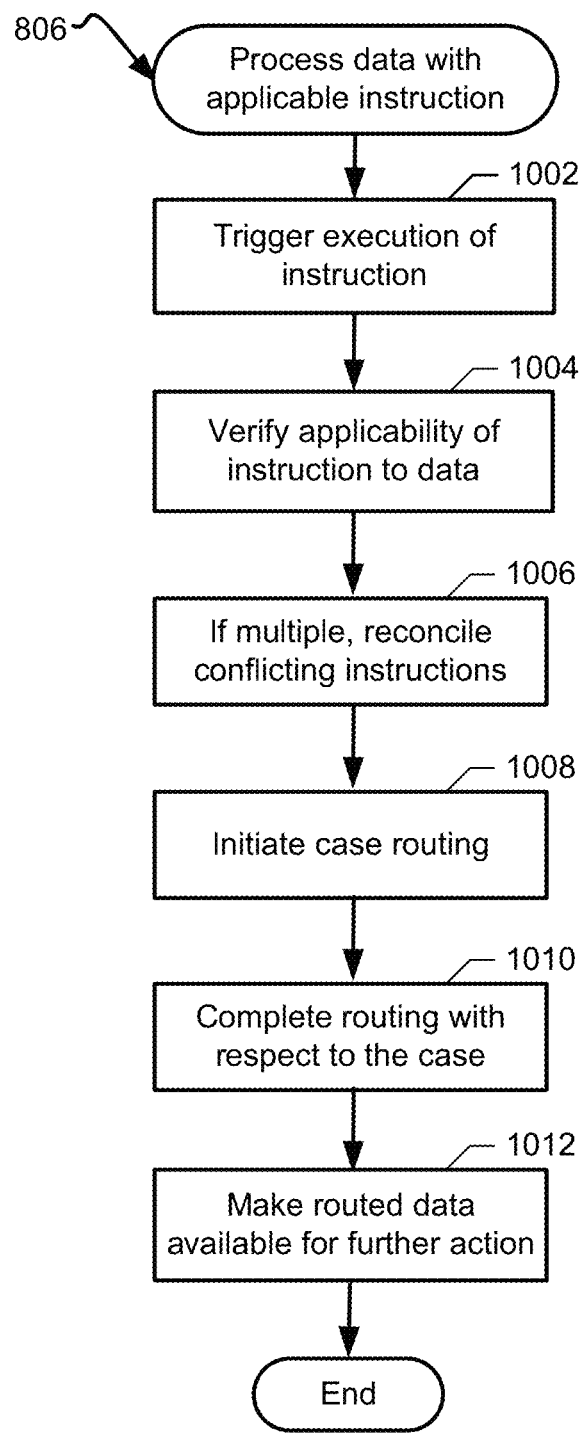

Flowcharts representative of example machine readable instructions for implementing and/or executing in conjunction with the example systems, algorithms, and interfaces of FIGS. 1-7B are shown in FIGS. 8-10. In these examples, the machine readable instructions comprise a program for execution by a processor such as the processor 1112 shown in the example processor platform 1100 discussed below in connection with FIG. 11. The program can be embodied in software stored on a tangible computer readable storage medium such as a CD-ROM, a floppy disk, a hard drive, a digital versatile disk (DVD), a BLU-RAY™ disk, or a memory associated with the processor 1112, but the entire program and/or parts thereof could alternatively be executed by a device other than the processor 1112 and/or embodied in firmware or dedicated hardware. Further, although the example program is described with reference to the flowcharts and/or processes illustrated in FIGS. 8-10, many other methods of implementing the examples disclosed and described here can alternatively be used. For example, the order of execution of the blocks can be changed, and/or some of the blocks described can be changed, eliminated, or combined.

As mentioned above, the example processes of FIG. 8-10 can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 8-10 can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 8 illustrates a flow diagram for an example method 800 to process incoming data at the cloud-based case creation and routing system 600. At block 802, a data source (e.g., a PACS, RIS, enterprise archive, electronic medical record, vendor neutral archive, incoming data stream from an imaging modality, etc.) is connected to the cloud-based platform 600 by the input data processor 610 via a gateway (e.g., edge device 310, 418, etc.). In some examples, a plurality of gateways are available, and a user and/or application at the data source can select a gateway to connect to the cloud-based system 600. The input data processor 610 can process the input data to identify a type, quantity, and/or other characteristic(s) of the incoming data (e.g., by evaluating metadata, header information, etc., associated with the input data from the data source).

At block 804, once the data source is connected to the platform 600, available instructions (e.g., stored in the repository 625 of the data store 620, etc.) are evaluated by the instruction processor 630 to determine which available instruction(s) apply to the input data. For example, applicable instruction(s) can be displayed for user selection via the interface 700, 750, automatically applied to the data to trigger the case creator 640 and/or case router 650, etc.

At block 806, the input data is processed according to one or more applicable instructions. For example, a user can select one or more instructions from the interface 700, 750 to apply to the data and/or the instruction processor 630 can automatically select and apply instruction(s) to trigger the case creator 640 to create a new case and/or the case router 650 to route the data for an existing case, etc.

At block 808, the cloud-based platform 600 is updated based on the processing of the data. For example, a record or reference to a new case can be saved in the data store 620, a new and/or edited instruction can be saved in the repository 625, an updated case can be reflected in the data store 620, etc.

FIG. 9 illustrates a flow diagram providing further detail regarding an example implementation of processing the data according to an applicable instruction (block 806). At block 902, execution of an instruction is triggered (e.g., by user selection and/or by automatic determination) to create a new case. At block 904, applicability of the instruction to the data is verified. For example, a type and/or other applicability criterion (e.g., location, role, group, user, service, etc.), other condition (e.g., modality, referring physician name, study description, performing physician name, patient age, etc.), etc., is verified to confirm that the case creation instruction is applicable to the input data.

At block 906, case creation is initiated. For example, the input data is used to create a new case based on the rules saved to define the format (e.g., available fields, data type(s), etc.), parameters (e.g., privacy, priority, etc.), applicability (e.g., location, role, group, user, service, etc.), corresponding clinical reason (e.g., collaboration, historical patient information, multi-disciplinary team meeting, off-hour read, patient transfer, second opinion, protocol, legal request, trauma transfer, etc.), etc.

At block 908, the case is configured. For example, search criteria such as patient identifier, case identifier, modality, referring physician name, study description, performing physician name, patient age, etc., can be established based on the instruction to allow the case to be searched, grouped, indexed, etc. The case can be indexed for location for future data routing, etc. The case can be associated with one or more users, locations, types, other cases, etc.

At block 910, the input data is associated with the case. For example, the created case is populated with the input data, etc. At block 912, the case is stored. For example, the case and/or a reference to the case can be stored in the cloud data store 620, etc. At block 914, the case is made available for further action such as search/query, routing, supplementing, etc.

FIG. 10 illustrates a flow diagram providing further detail regarding another example implementation of processing the data according to an applicable instruction (block 806). At block 1002, execution of an instruction is triggered (e.g., by user selection and/or by automatic determination) to route the data with respect to an existing case. At block 1004, applicability of the instruction to the data is verified. For example, an intended recipient, type and/or other applicability criterion (e.g., recipient, location, role, group, user, service, etc.), etc., is verified to confirm that the case routing instruction is applicable to the input data. At block 1006, if multiple conflicting instructions are applicable to the data, then the conflict is arbitrated to select an instruction that controls (e.g., based on priority, etc.).

At block 1008, case routing is initiated. For example, the intended recipient of the routing can be identified from the routing instruction, and routing and/or download information can dictate whether the input data is routed to another system, downloaded to a local system, etc. For example, the data can be routed to another person or group, reconciled and downloaded to a PACS, directly downloaded to a PACS, etc. At block 1010, case routing (e.g., routing and/or download, etc.) is completed. For example, confirmation of reconciliation, download, other routing, etc., is made, and, at block 1012, the routed data is made available at the target system (e.g., a PACS, RIS, imaging desktop, etc., for further action such as image reading, computer-aided diagnosis, further examination, etc.

V. Computing Device

The subject matter of this description may be implemented as stand-alone system or for execution as an application capable of execution by one or more computing devices. The application (e.g., webpage, downloadable applet or other mobile executable) can generate the various displays or graphic/visual representations described herein as graphic user interfaces (GUIs) or other visual illustrations, which may be generated as webpages or the like, in a manner to facilitate interfacing (receiving input/instructions, generating graphic illustrations) with users via the computing device(s).

Memory and processor as referred to herein can be stand-alone or integrally constructed as part of various programmable devices, including for example a desktop computer or laptop computer hard-drive, field-programmable gate arrays (FPGAs), application-specific integrated circuits (ASICs), application-specific standard products (ASSPs), system-on-a-chip systems (SOCs), programmable logic devices (PLDs), etc. or the like or as part of a Computing Device, and any combination thereof operable to execute the instructions associated with implementing the method of the subject matter described herein.

Computing device as referenced herein can include: a mobile telephone; a computer such as a desktop or laptop type; a Personal Digital Assistant (PDA) or mobile phone; a notebook, tablet or other mobile computing device; or the like and any combination thereof.

Computer readable storage medium or computer program product as referenced herein is tangible (and alternatively as non-transitory, defined above) and can include volatile and non-volatile, removable and non-removable media for storage of electronic-formatted information such as computer readable program instructions or modules of instructions, data, etc. that may be stand-alone or as part of a computing device. Examples of computer readable storage medium or computer program products can include, but are not limited to, RAM, ROM, EEPROM, Flash memory, CD-ROM, DVD-ROM or other optical storage, magnetic cassettes, magnetic tape, magnetic disk storage or other magnetic storage devices, or any other medium which can be used to store the desired electronic format of information and which can be accessed by the processor or at least a portion of the computing device.

The terms module and component as referenced herein generally represent program code or instructions that causes specified tasks when executed on a processor. The program code can be stored in one or more computer readable mediums.

Network as referenced herein can include, but is not limited to, a wide area network (WAN); a local area network (LAN); the Internet; wired or wireless (e.g., optical, Bluetooth, radio frequency (RF)) network; a cloud-based computing infrastructure of computers, routers, servers, gateways, etc.; or any combination thereof associated therewith that allows the system or portion thereof to communicate with one or more computing devices.

The term user and/or the plural form of this term is used to generally refer to those persons capable of accessing, using, or benefiting from the present disclosure.

Figure 11:
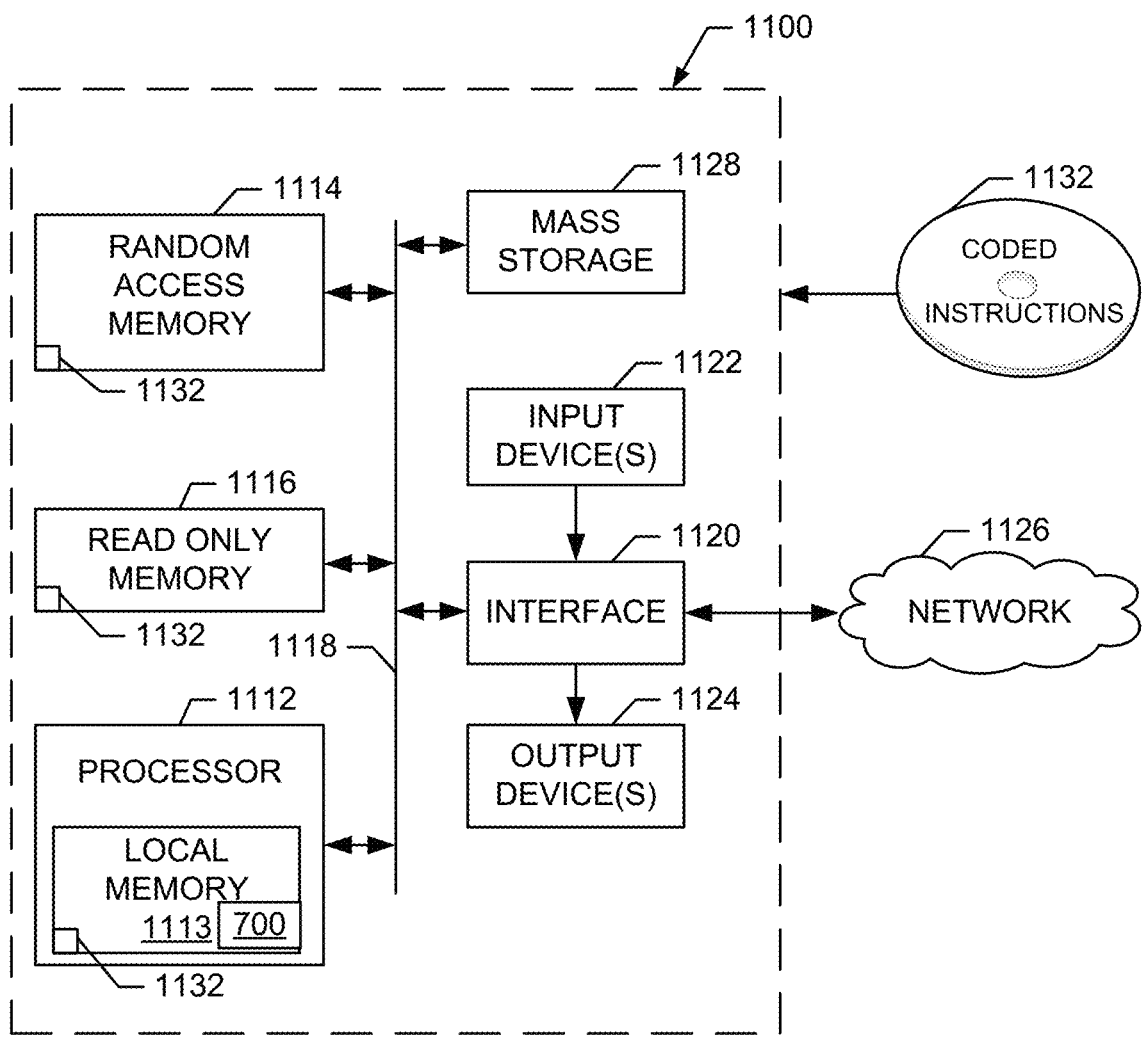
FIG. 11 shows a block diagram of an example processor system that can be used to implement systems and methods described herein.

FIG. 11 is a block diagram of an example processor platform 1100 capable of executing instructions to implement the example systems and methods disclosed and described herein. The processor platform 1100 can be, for example, a server, a personal computer, a mobile device (e.g., a cell phone, a smart phone, a tablet such as an IPAD™), a personal digital assistant (PDA), an Internet appliance, or any other type of computing device.

The processor platform 1100 of the illustrated example includes a processor 1112. The processor 1112 of the illustrated example is hardware. For example, the processor 1112 can be implemented by one or more integrated circuits, logic circuits, microprocessors or controllers from any desired family or manufacturer.

The processor 1112 of the illustrated example includes a local memory 1113 (e.g., a cache). The processor 1112 of the illustrated example is in communication with a main memory including a volatile memory 1114 and a non-volatile memory 1116 via a bus 1118. The volatile memory 1114 can be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1116 can be implemented by flash memory and/or any other desired type of memory device. Access to the main memory 1114, 1116 is controlled by a memory controller.

The processor platform 1100 of the illustrated example also includes an interface circuit 1120. The interface circuit 1120 can be implemented by any type of interface standard, such as an Ethernet interface, a universal serial bus (USB), and/or a PCI express interface.

In the illustrated example, one or more input devices 1122 are connected to the interface circuit 1120. The input device(s) 1122 permit(s) a user to enter data and commands into the processor 1112. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1124 are also connected to the interface circuit 1120 of the illustrated example. The output devices 1124 can be implemented, for example, by display devices (e.g., a light emitting diode (LED), an organic light emitting diode (OLED), a liquid crystal display, a cathode ray tube display (CRT), a touchscreen, a tactile output device, a light emitting diode (LED), a printer and/or speakers). The interface circuit 1120 of the illustrated example, thus, typically includes a graphics driver card, a graphics driver chip or a graphics driver processor.

The interface circuit 1120 of the illustrated example also includes a communication device such as a transmitter, a receiver, a transceiver, a modem and/or network interface card to facilitate exchange of data with external machines (e.g., computing devices of any kind) via a network 1126 (e.g., an Ethernet connection, a digital subscriber line (DSL), a telephone line, coaxial cable, a cellular telephone system, etc.).

The processor platform 1100 of the illustrated example also includes one or more mass storage devices 1128 for storing software and/or data. Examples of such mass storage devices 1128 include floppy disk drives, hard drive disks, compact disk drives, Blu-ray disk drives, RAID systems, and digital versatile disk (DVD) drives.

The coded instructions 1132 can be stored in the mass storage device 1128, in the volatile memory 1114, in the non-volatile memory 1116, and/or on a removable tangible computer readable storage medium such as a CD or DVD. The instructions 1132 can be executed by the processor 1112 to implement the example clinical case creation and routing automation system 600, etc., as disclosed and described above.

From the foregoing, it will be appreciated that example methods, apparatus and articles of manufacture have been disclosed that enable automated clinical case creation and routing. The disclosed methods, apparatus and articles of manufacture improve operation of a computing device and cloud-based system driven by the computing device through a cloud-based medical image and document exchange infrastructure. Certain examples improve a computer system and its process and interaction through an intelligent, automated analysis of incoming data, active instructions, and associated rules through new instruction data structures and cloud-based processing, creation, storage, and routing of clinical data. While prior approaches did not provide such case creation and routing, certain examples alter the operation of the computing device and provide a new infrastructure for clinical case processing, maintenance, and flexible, dynamic control with respect to incoming data. The disclosed methods, apparatus and articles of manufacture are accordingly directed to one or more improvement(s) in the functioning of a computer, as well as a new data structure and method of clinical case processing and management.

Certain examples provide clinical case automation creation to automatically generate a new case and allocate that case to a clinician's workflow. Certain examples provide clinical case routing automation for existing cases already created, to take action with respect to a case using instructions to download, forward, and/or otherwise process data related to the case based on certain rule(s), criterion(-ia), etc., defined in the instruction. Certain examples provide an infrastructure to facilitate data sharing by executing instruction(s) with respect to a clinical case. Certain examples integrate orders and associated actions with respect to a case and automated instruction execute to generate one-click transmission, processing, and update of image data and associated reports and results.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A cloud-based medical image and document exchange infrastructure apparatus comprising:
    an instruction processor to execute instructions to process data according to one or more defined conditions, wherein each instruction is associated with a respective state, the state including at least active and inactive, a value of the state to trigger inclusion of an active instruction and exclusion of an inactive instruction from comparison to data; and
    a gateway to at least:
        receive incoming data related to an imaging study;
        monitor the incoming data to compare the incoming data to one or more active instructions according to one or more associated rules; and
        when at least one of the one or more active instructions applies to the incoming data, execute the at least one active instruction with respect to the incoming data and the corresponding imaging study to automatically at least:
            create a case at a first system using the incoming data according to the at least one active instruction;
            register the case with respect to a patient and the first system;
            route the case to a clinician according to the at least one active instruction to trigger a clinician workflow for the clinician involving the case and a device associated with the workflow.

2. The apparatus of claim 1, wherein the case is an existing case, and wherein the active instruction is to route the incoming data with respect to the existing case to be at least one of reconciled and downloaded to a target device or downloaded to the target device.

3. The apparatus of claim 1, wherein the case is a new clinical case, and wherein the active instruction is to create the new clinical case, associate with incoming data with the new clinical case, and make the new clinical case available for search and filtering via an interface.

4. The apparatus of claim 1, wherein the active instruction is defined by metadata, the metadata to be compared by the gateway to the incoming data associated with an imaging study.

5. The apparatus of claim 1, wherein a created instruction is to be inactive until the created instruction is associated with the gateway, and wherein the created instruction is then to be activated through an action of a user.

6. The apparatus of claim 1, wherein the gateway is an edge device connecting a local data source to a cloud platform.

7. The apparatus of claim 1, further including an instruction generator to facilitate generation of instructions to be searchable and executable by the instruction processor with respect to the incoming data.

8. The apparatus of claim 1, wherein the gateway is to execute the at least one active instruction to automatically create, register, and route the case in response to a single action at an interface.

9. The apparatus of claim 1, wherein the at least one active instruction triggers a collaboration between the clinician and another user via the apparatus for at least one of diagnosis or treatment of the patient with respect to the case.

10. The apparatus of claim 1, wherein the at least one active instruction is to add activity to a log tracking a sequence of events associated with the case.

11. A computer-readable storage medium including instructions that, when executed, cause at least one processor to at least:

receive incoming data related to an imaging study;

monitor the incoming data to compare the incoming data to one or more active instructions according to one or more associated rules, each instruction to process data according to one or more defined conditions, each instruction associated with a state including at least active and inactive, a value of the state to trigger inclusion of an active instruction and exclusion of an inactive instruction from comparison to data; and when at least one of the one or more active instructions applies to the incoming data, execute the at least one active instruction with respect to the incoming data and the corresponding imaging study to automatically at least:

create a case at a first system using the incoming data according to the at least one active instruction;

register the case with respect to a patient and the first system;

route the case to a clinician according to the at least one active instruction to trigger a clinician workflow for the clinician involving the case and a device associated with the workflow.

12. The computer-readable storage medium of claim 11, wherein the case is an existing case, and wherein the active instruction is to route the incoming data with respect to the existing case to be at least one of reconciled and downloaded to a target device or downloaded to the target device.

13. The computer-readable storage medium of claim 11, wherein the case is a new clinical case, and wherein the active instruction is to create the new clinical case, associate with incoming data with the new clinical case, and make the new clinical case available for search and filtering via an interface.

14. The computer-readable storage medium of claim 11, wherein the active instruction is defined by metadata, the metadata to be compared to the incoming data associated with an imaging study.

15. The computer-readable storage medium of claim 11, wherein a created instruction is to be inactive until the created instruction is associated with a gateway, and wherein the created instruction is then to be activated through an action of a user.

16. The computer-readable storage medium of claim 15, wherein the activated created instruction is to be searchable and executable with respect to the incoming data.

17. A computer-implemented method comprising:

receiving, by executing an instruction using at least one processor, incoming data related to an imaging study;

monitoring, by executing an instruction using the at least one processor, the incoming data to compare the incoming data to one or more active instructions according to one or more associated rules, each instruction to process data according to one or more defined conditions, each instruction associated with a state including at least active and inactive, a value of the state to trigger inclusion of an active instruction and exclusion of an inactive instruction from comparison to data; and when at least one of the one or more active instructions applies to the incoming data, executing the at least one active instruction using the at least one processor with respect to the incoming data and the corresponding imaging study to automatically at least:

create a case at a first system using the incoming data according to the at least one active instruction;

register the case with respect to a patient and the first system;

route the case to a clinician according to the at least one active instruction to trigger a clinician workflow for the clinician involving the case and a device associated with the workflow.

18. The method of claim 17, wherein the case is an existing case, and wherein the active instruction is to route the incoming data with respect to the existing case to be at least one of reconciled and downloaded to a target device or downloaded to the target device.

19. The method of claim 17, wherein the case is a new clinical case, and wherein the automated case creation instruction is to create the new clinical case, associate with incoming data with the new clinical case, and make the new clinical case available for search and filtering via an interface.

20. The method of claim 17, wherein a created instruction is to be inactive until the created instruction is associated with a gateway, and wherein the created instruction is then to be activated through an action of a user.

* * * * *